US009625364B2

(12) United States Patent
Hodgson et al.

(10) Patent No.: US 9,625,364 B2
(45) Date of Patent: Apr. 18, 2017

(54) NON-RADIOACTIVE DENSITY MEASUREMENT IN OILFIELD OPERATIONS

(75) Inventors: Kim A. Hodgson, Sugar Land, TX (US); Yannick William Fouagou, Garoua (CM)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 1096 days.

(21) Appl. No.: 13/638,889

(22) PCT Filed: Mar. 28, 2011

(86) PCT No.: PCT/IB2011/051307
§ 371 (c)(1),
(2), (4) Date: Oct. 25, 2013

(87) PCT Pub. No.: WO2011/121524
PCT Pub. Date: Oct. 6, 2011

(65) Prior Publication Data
US 2014/0041451 A1    Feb. 13, 2014

Related U.S. Application Data

(60) Provisional application No. 61/319,417, filed on Mar. 31, 2010.

(51) Int. Cl.
*G01N 9/04* (2006.01)
*G01N 9/36* (2006.01)
*G01N 15/06* (2006.01)

(52) U.S. Cl.
CPC ............... *G01N 9/04* (2013.01); *G01N 9/36* (2013.01); *G01N 15/06* (2013.01)

(58) Field of Classification Search
CPC ............. G01N 9/04; G01N 9/36; G01N 15/06
(Continued)

(56) References Cited

U.S. PATENT DOCUMENTS 2,613,530 A * 10/1952 Nichols .................... G01N 9/06
177/178
3,583,505 A * 6/1971 Van Valkinburgh ..... G01G 3/02
177/232

(Continued)

FOREIGN PATENT DOCUMENTS

| CA | 2680355 C | 3/2008 |
| WO | 2011121524 A2 | 10/2011 |

OTHER PUBLICATIONS

International Search Report, Application No. PCT/IB2011/051307 filed Mar. 28, 2011, dated Dec. 26, 2011.
Model DB-II Pneumatic Densimeter, Operating Manual S-102, Byron Jackson Inc., Petroleum Equipment and Service Division, Aug. 15, 1969, Long Beach, California.
(Continued)

*Primary Examiner* — Daniel S Larkin
*Assistant Examiner* — Anthony W Megna Fuentes
(74) *Attorney, Agent, or Firm* — Michael L. Flynn

(57) ABSTRACT

The current application discloses a non-contact, non-radioactive densitometer system, comprising a curved tube containing an oilfield fluid, a mass measuring device connected to the curved tube, and a data acquisition system connected to the mass measuring device. The mass measuring device measures the mass of the curved tube and the data acquisition system calculate the density of the oilfield fluid in the curved tube. In one embodiment, the non-contact, non-radioactive densitometer system further comprises an antilog amplifier that is connected between the mass measuring device and the data acquisition system, where the antilog amplifier transforms the mass of the curved tube into an exponential value which is then fed into the data acquisition system.

16 Claims, 3 Drawing Sheets

(58) Field of Classification Search
USPC .................................................. 73/433, 434
See application file for complete search history.

(56) References Cited

U.S. PATENT DOCUMENTS

| | | | |
|---|---|---|---|
| 4,353,482 | A | 10/1982 | Tomlinson et al. |
| 4,779,186 | A | 10/1988 | Handke et al. |
| 6,581,451 | B2 * | 6/2003 | Ence ........................ G01N 9/04 73/149 |
| 7,249,500 | B2 | 7/2007 | Dutton et al. |
| 7,290,447 | B1 | 11/2007 | Burnette et al. |
| 7,387,159 | B2 | 6/2008 | Fitzgerald |
| 7,659,828 | B2 | 2/2010 | Wehrs et al. |
| 2004/0007059 | A1 | 1/2004 | Tudor |
| 2007/0262818 | A1 * | 11/2007 | Lee ........................ H03G 1/0029 330/278 |
| 2008/0115577 | A1 | 5/2008 | Headrick |
| 2012/0203463 | A1 | 8/2012 | Guo et al. |

OTHER PUBLICATIONS

Benabdelkarim et al., Nonradioactive Densitometer for Continuous Monitoring of Cement Mixing Process, SPE 23262, 1991, pp. 539-545.
Office Action issued in Canadian Patent Application No. 2,793,775 on Oct. 12, 2016; 4 pages.
Benadelkarim et al., "Nonradioactive Densitometer for Continuous Monitoring of Cement Mixing Process", SPE 23262, First International Conference on Health, Safety and Environment, Nov. 10-14, 1991, pp. 539-545.

* cited by examiner

Density

Density

NON-RADIOACTIVE DENSITY MEASUREMENT IN OILFIELD OPERATIONS

FIELD OF THE APPLICATION

The current application is generally related to measuring the density of an oilfield fluid during an oilfield operation, although embodiments disclosed herein may be applicable in other fields as well.

BACKGROUND

The statements in this section merely provide background information related to the present disclosure and may not constitute prior art.

In oilfield operations such as sand control, it is generally desirable to constantly monitor the density of an oilfield fluid (such as proppant slurries) being pumped into the well. One approach to achieve this is to use a contact-based densitometer to directly measure the oilfield fluid being passed through a pipe or a container. The flow rate of the oilfield fluid is measured and the density of the oilfield fluid is then calculated. Equipment in this category includes, but is not limited to, mass flowmeters, hydrometers, etc. However, because the equipment is directly exposed to the oilfield fluid being measured, it is often susceptible for failure during oilfield operations due to the highly corrosive or highly abrasive nature of oilfield fluids.

Another approach is by using a non-contact densitometer to indirectly measure the oilfield fluid in a pipe or a container during an oilfield operation. The most widely used equipment in this category is the radioactive densitometer. It typically comprises a radiation source (such as radioactive cesium or cobalt) and a radiation detector. The radiation source is positioned on one side of a pipe or container and the radiation detector is positioned on the other side of the pipe or container. The radiation source emits radiation waves (such as gamma rays) and the radiation detector measures the attenuation of the radiation waves after they pass through the oilfield fluid. A processor then calculates the density of the oilfield fluid based on the signal detected. During the entire procedure, the radioactive densitometer does not contact the oilfield fluid being measured, hence the name "non-contact" densitometer.

One major disadvantage associated with using radioactive densitometers is the stringent regulations imposed by the government of various jurisdictions on the proper handling, transportation and storage of radioactive materials used in the radioactive densitometer. Accordingly, efforts have been made to use non-radioactive system to measure the density of oilfield fluids. For example, in one article, a Coriolis mass flowmeter was used to measure fluid densities. SPE23262, "Nonradioactive Densitometer for Continous Monitoring of Cement Mixing Process" (1991). However, the measuring tube in the Coriolis mass flowmeter can be eroded very quickly when the abrasive proppant slurries are pumped at a high rate through the flowmeter. Moreover, when the oilfield operation is to be conducted at high rates (such as 30 BPM) and/or involving tubes with big diameters (such as 6 inches or higher), the Coriolis mass flowmeter quickly becomes large in size and highly expensive.

US Patent Application Publication No. 2008/0115577 discloses a method of manufacturing a high pressure vibrating tube densitometer comprising enclosing twin flow tubes within an outer shell where the outer shell comprises portals for the installation or replacement of internal components.

US Patent Application Publication No. 2004/0007059 discloses a method of determining the concentration of a particulate added to a fluid stream comprising the steps of measuring the rate of flow of the fluid stream, determining the rate of particulate flow by using an acoustic sensor and then calculating the concentration of the particulate in the fluid stream using results from the measuring and determining steps.

There remains a need for a non-contact, non-radioactive densitometer that solves one or more of the above identified problems.

SUMMARY

According to one aspect, there is provided a non-contact, non-radioactive densitometer system comprising a curved tube containing an oilfield fluid, a mass measuring device connected to the curved tube, and a data acquisition system connected to the mass measuring device. The mass measuring device measures the mass of the curved tube and the data acquisition system calculate the density of the oilfield fluid in the curved tube.

In one embodiment, the non-contact, non-radioactive densitometer system further comprises an antilog amplifier that is connected between the mass measuring device and the data acquisition system so that the antilog amplifier can transform the mass of the curved tube into an exponential value which is then fed into the data acquisition system.

In one embodiment, the non-contact, non-radioactive densitometer system transforms the mass of the curved tube into the exponential value by applying the following equation:

$$I_{out} = a \times \mathrm{Exp}(b \times m_{of}) \quad \text{(Equation III)}$$

wherein,
$I_{out}$ is a signal output from the antilog amplifier;
a and b are constants;
$m_{of}$ is the mass of the curved tube filled with the oilfield fluid minus the mass of the curved tube when empty.

The oilfield fluid can be proppant slurry. The curved tube can be substantially in the form of a "U" or "V" shape. Moreover, the curved tube may occupy a substantially horizontal plane. The mass measuring device can be a load cell such as an extension load cell. In one embodiment, the extension load cell is connected to a tripod on one end and to the curved tube on the other end.

According to another aspect, there is provided a method for measuring a density of an oilfield fluid. The method comprises providing a curved tube at an oilfield, filling the curved tube with an oilfield fluid, measuring the mass of the curved tube filled with the oilfield fluid, and calculating the density of the oilfield fluid. In one embodiment, the method further comprises conducting an exponential transformation of the mass of the curved tube filled with the oilfield fluid before calculating the density of the oilfield fluid, where the exponential transformation is performed by applying Equation III above.

According to another aspect of the application, there is provided a non-contact, non-radioactive densitometer apparatus, comprising a curved tube, a load cell connected to the curved tube, and a computer system connected to the mass measuring device. The load cell measures the mass of the curved tube and the data computer system calculate the density of an oilfield fluid contained in the curved tube.

In one embodiment, the non-contact, non-radioactive densitometer apparatus further comprises an antilog amplifier that is connected between the load cell and the computer system, where the antilog amplifier transforms the mass of the curved tube into an exponential value which is then fed into the data acquisition system. In one case, the exponential transformation is performed by applying the following Equation III above.

BRIEF DESCRIPTION OF THE DRAWINGS

These and other features and advantages will be better understood by reference to the following detailed description when considered in conjunction with the accompanying drawings.

DETAILED DESCRIPTION OF SOME ILLUSTRATIVE EMBODIMENTS

Figure 1:
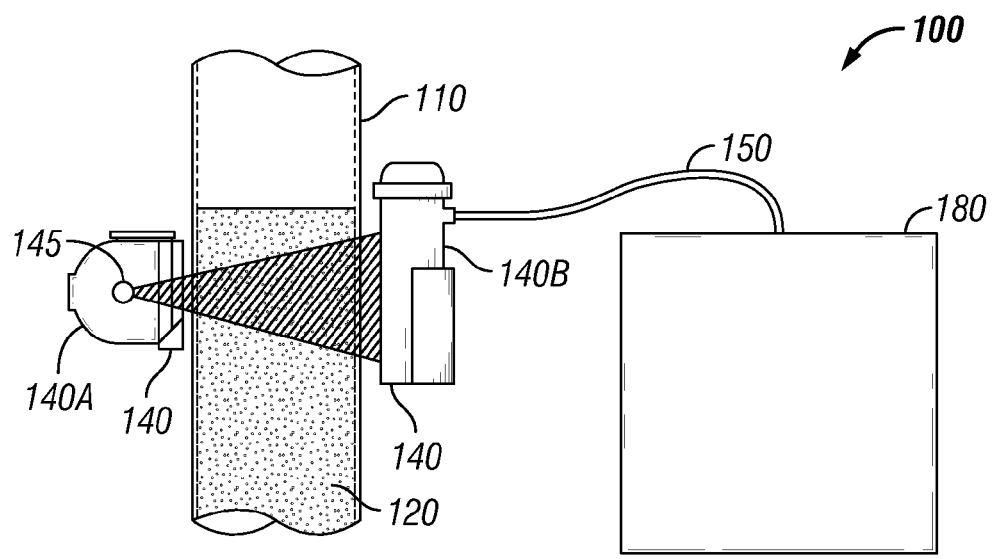
FIG. 1 is a schematic illustration of a prior art system utilizing a radioactive densitometer to measure the density of a target oilfield fluid.

For the purposes of promoting an understanding of the principles of the current application, reference will now be made to the embodiments illustrated in the drawings and specific language will be used to describe the same. It will nevertheless be understood that no limitation of the scope of the application is thereby intended, any alterations and further modifications in the illustrated embodiments, and any further applications of the principles of the system, apparatus, and method as illustrated therein as would normally occur to one skilled in the art to which the current application relates are contemplated herein.

FIG. 1 shows a prior art system 100 where a radioactive densitometer 140 is used. As illustrated, the radioactive densitometer 140 may comprise a source component 140A and a detection component 140B. The source component 140A may contain one or more radioactive sources material 145, such as radioactive cesium or cobalt, and is positioned on one side of a pipe 110 through which an oilfield fluid 120 is delivered. The detection component 140B may contain one or more radioactive detectors and is positioned on the other site of the pipe 110 so that the radioactive signal emitted from the source component 140A can be detected by the detection component 140B after the signal is attenuated by the pipe 110 and the oilfield fluid 120. The detected signal can then be fed into a data acquisition system 180 such as a computer via a cable 150, where the density of the oilfield fluid 120 can be calculated and displayed.

Figure 2:
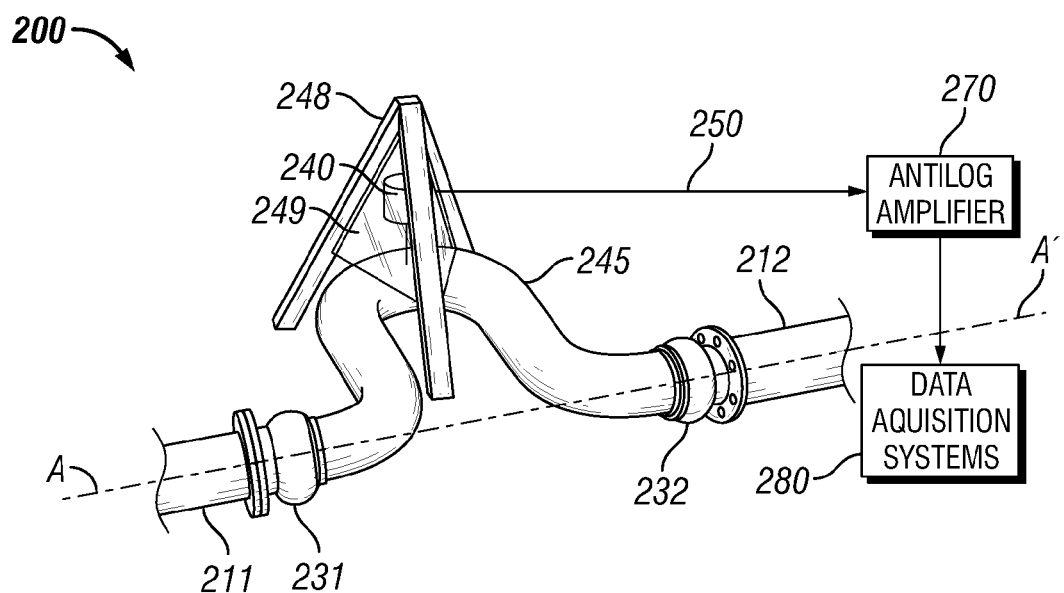
FIG. 2 is a schematic illustration of a non-contact, non-radioactive densitometer system according to one embodiment of the current application.
Figure 3:
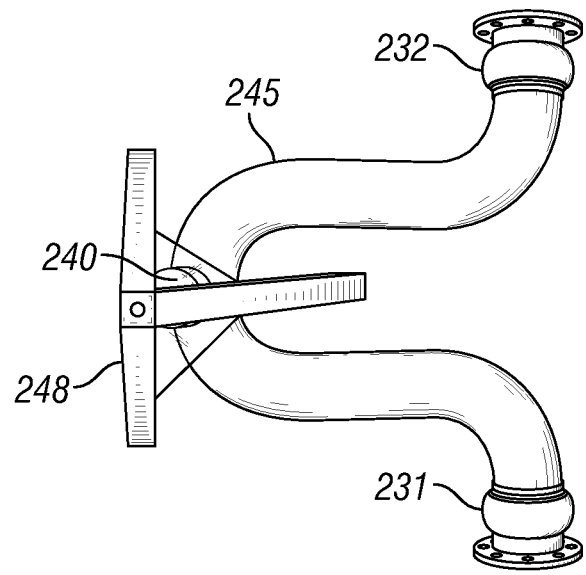
FIG. 3 is a schematic illustration of a perspective view from the top of the non-contact, non-radioactive densitometer system according to one embodiment of the current application.
Figure 4:
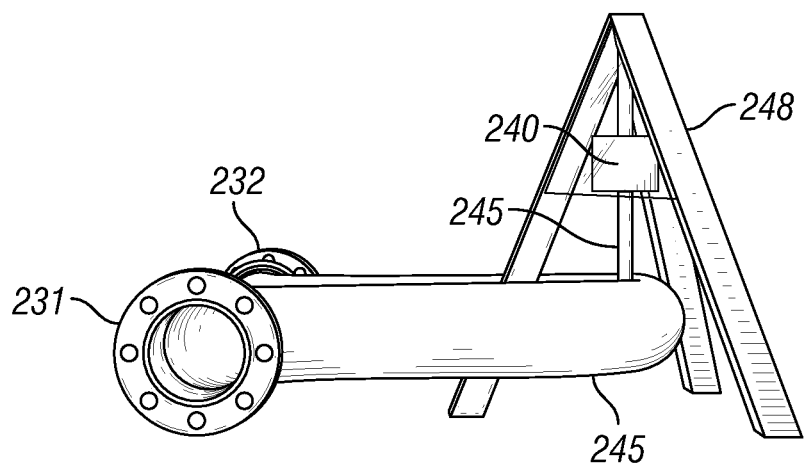
FIG. 4 is a schematic illustration of a perspective view from the side of the non-contact, non-radioactive densitometer system according to one embodiment of the current application.

FIGS. 2-4 illustrate an exemplary non-contact, non-radioactive densitometer according to one aspect of the current application. System 200 comprises a curved tube 245, a mass measuring device 240 that is connected to the curved tube 245 and measures the mass of the curved tube 245, an antilog amplifier 270 that is connected to the mass measuring device 240 and transforms the data detected by the mass measuring device 240 from a linear curve to an exponential curve, and a data acquisition system 280 that is connected to the antilog amplifier 270 and calculates the density of the oilfield fluid that is contained in the curved tube 245.

As used in the current application, the term "fluid" should be constructed broadly to include any medium that is continuous and amorphous whose molecules are capable of moving freely past one another and that has the tendency to assume the shape of its container. A fluid can be a liquid, a gas, or a mixture thereof, which may further contain solids or solid particles suspended therein. Furthermore, as used in the current application, the term "oilfield fluid" should be interpreted broadly to include any fluid that may exist or be used at an oilfield during an oilfield operation, including, but not limited to, drilling, cementing, logging, stimulation, completion, production, and so on. Examples of "oilfield fluids" in the current application include, but are not limited to, proppant slurries, cement slurries, drilling fluids (often referred to as "mud"), hydraulic fracturing fluids, acid stimulation fluids, production fluids, and so on. In some cases, the fluid or oilfield fluid is air. In some other case, the fluid or oilfield fluid is water. In some further cases, the fluid or oilfield fluid is the cement slurry used in a cementing operation in the oilfield.

In the illustrated embodiment in FIGS. 2-4, the curved tube 245 is substantially in the form of a "U" shape. However, the curved tube 245 can be substantially in the form of a "V" shape or other shapes readily perceivable by people skilled in the art after reviewing the disclosure of the current application. Moreover, in some cases, the mass measuring device 240 is connected to the substantially mid-point of curved tube 245. In some other cases, the mass measuring device 240 is connected to the curved tube 245 at a point that is substantially away from the mid-point of curved tube 245.

In the embodiment illustrated in FIGS. 2-4, the mass measuring device 240 is an extension load cell such as the 300 lbs Canister Load Cells that is supported by a tripod 248. However, it should be noted that other mass measuring devices such as spring scale and other supporting structure such as box frames or crossbars can also be used without departing from the teaching of the current application. In the embodiment illustrated in FIGS. 2-4, the extension load cell 240 can be positioned directly underneath the juncture of the three legs of the tripod 248. The mid-point of the curved tube 245 can be positioned directly underneath the extension load cell 240. In such a way, the juncture of the three legs of the tripod 248, the extension load cell 240, and the mid-point of curved tube 245 are substantially aligned with each other in the vertical direction.

Optionally, the tripod 248 may further comprise one or more covers 249 disposed between adjacent legs so that a hollow pyramidal space can be created in the tripod 248. The extension load cell 240 can be positioned inside the hollow pyramidal space, so that the potential impact by external factors (such as winds) on the extension load cell 240 can be minimized. In one particular example, the cover 249 is made of a transparent material, such as glass or clear plastic, so that the load cell can be readily inspected by a field operator from the outside of the tripod 248.

In another alternative embodiment, the mass measuring device 240 is a scale (not shown), a compression load cell (not shown), or any other devices that can measure the mass of an object resting on top of it. Therefore, the mass measuring device 240 in this embodiment can be placed underneath the curved tube 245 and measures the mass of the curved tube 245 from the bottom of the curved tube 245 instead of from the top, as in the case of using the extension load cell 240 as discussed above.

In one embodiment, an upstream pipe 211 is connected to a first end of the curved tube 245 via a first swivel joint 231, and a downstream pipe 212 is connected to a second end of the curved tube 245 via a second swivel joint 232. One example of the swivel joint is Chiksan® Series 2000 Swivel Joint—Carbon Steel, although other swivel joints can be used in the current application as well. After the connection, the curved tube 245 can rotate freely (or with little friction) along the longitudinal axis A-A' defined by the upstream pipe 211 and downstream pipe 212. Therefore, the mass measuring device 240 is capable of measuring the mass equivalent of the torque that is created on the curved tube 245 with swivels on both ends.

The diameter of the curved tube 245 can be the same as the diameter of the upstream pipe 211 or downstream pipe 212, so as to minimize the potential impact by the change of flow path diameters to the reading of the mass measuring device 240. Alternatively, the diameter of the curved tube 245 can be different from the diameter of the upstream pipe 211 or downstream pipe 212, depending on the particular setting of an oilfield operation.

In some cases, the curved tube 245 can be made of the same material as that of the upstream pipe 211 or downstream pipe 212. In some other cases, the curved tube 245 can be made of a material that is of higher quality than that of the upstream pipe 211 or downstream pipe 212. Therefore, the corrosion resistivity, anti-washout capability, etc. of the curved tube 245 are the same as or higher than those of the upstream pipe 211 or downstream pipe 212, so that the lifespan of the curved tube 245 is at least the same as that of the upstream pipe 211 or downstream pipe 212. Other variations are possible depending on the particular setting of an oilfield operation.

In one embodiment, the curved tube 245 is positioned to occupy a substantially horizontal plane, best seen in FIG. 4. That is, the first end of the curved tube 245, the second end of the curved tube 245, and the mid-point of the curved tube 245 together define a plane that is substantially perpendicular to the gradient of the gravity field at the location of the oilfield operation. Alternatively, the curved tube 245 may be designed to occupy a plane that is tilted at an angle from the horizontal plane. All such variations are within the scope of the current application.

In operation, the volume of the curved pipe 245 can be determined by using the following equation:

$$V = [(m_{H2O} - m_{air})/(\rho_{H2O} - \rho_{air})] \qquad \text{(Equation I)}$$

wherein,
V is the volume of the curved pipe 245;
$m_{air}$ is the mass measured by the mass measuring device 240 when the curved pipe 245 is completely empty;
$m_{H2O}$ is the mass measured by the mass measuring device 240 when the curved pipe 245 is filled with pure water;
$\rho_{air}$ is the density of air; and
$\rho_{H2O}$ is the density of the pure water.
For simplicity, $\rho_{air}$ can be assumed to be zero pounds per gallon (PPG) and $\rho_{H2O}$ can be assumed to be 8.34 pounds per gallon (PPG).

With the volume of the curved pipe 245 properly determined, the density of the oilfield fluid can be calculated as follows:

$$\rho_{of} = m_{of}/V \qquad \text{(Equation II)}$$

wherein,
V is the volume of the curved pipe 245;
$m_{of}$ is the mass measured by the mass measuring device 240 when the curved pipe 245 is filled with an oilfield fluid minus the mass of the curved tube 245 when it is empty, e.g. $m_{air}$; and
$\rho_{of}$ is the density of the oilfield fluid.

To take advantage of the software and hardware currently used in the oilfield in association with the radioactive densitometer, in one further embodiment, the mass measuring device 240 is connected to an antilog amplifier 270 before it is connected to the data acquisition system 280, as illustrated in FIG. 2. Therefore, after the mass measuring device 240 obtains a reading on the mass of the curved tube 245, the mass measuring device 240 transmits the data to the antilog amplifier 270 where the data is transformed into an exponential value. For example, the data can be transformed by applying the following equation:

$$I_{out} = a \times \text{Exp}(b \times m_{of}) \qquad \text{(Equation III)}$$

wherein,
$I_{out}$ is the signal coming out of the antilog amplifier 270;
a and b are constants;
$m_{of}$ is the mass measured by the mass measuring device 240 when the curved pipe 245 is filled with an oilfield fluid minus the mass of the curved tube 245 when it is empty, e.g. $m_{air}$;

In one example, the antilog amplifier 270 is a Model AL500 Antilog Amplifier manufactured by Lee-Dickens Ltd. Other antilog amplifiers can be used in the current application as well.

Figure 5:
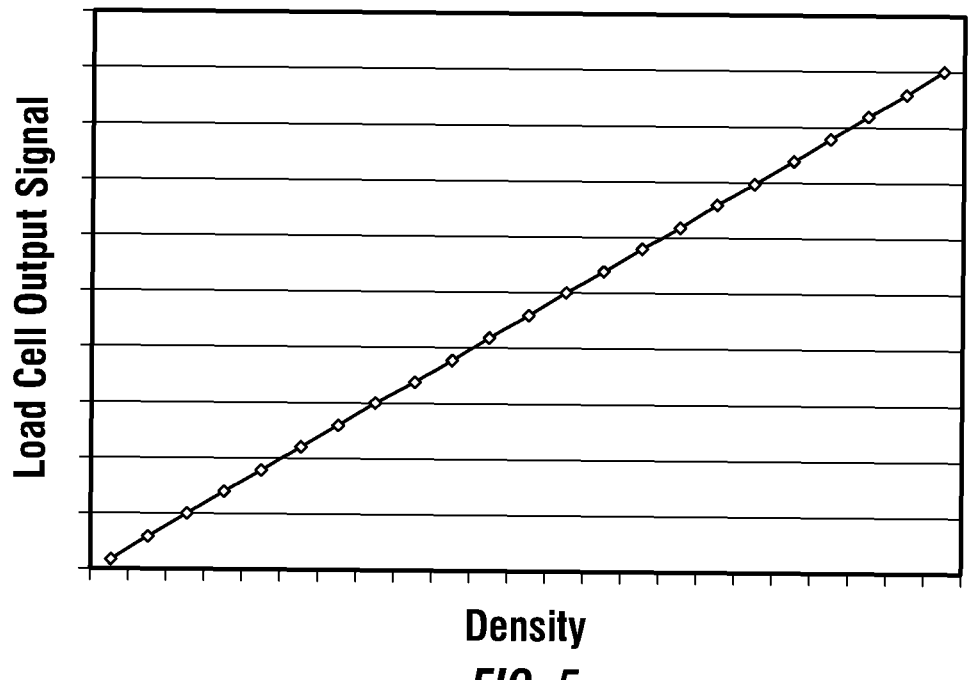
FIG. 5 is a schematic illustration of the data output of the load cell in relation to the density of the oilfield fluid being measured, according to one embodiment of the current application.
Figure 6:
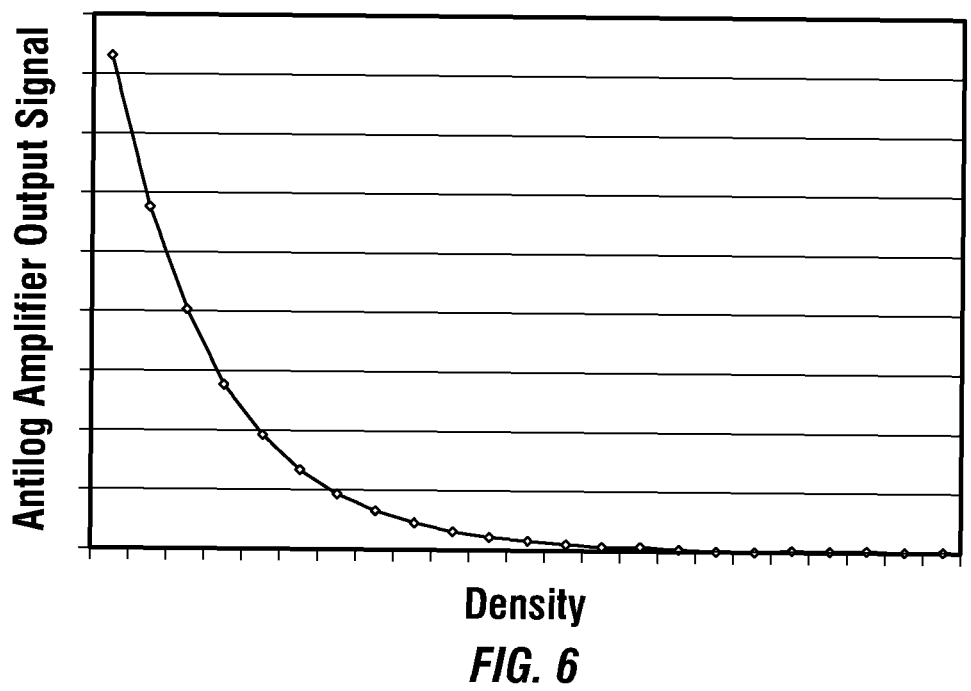
FIG. 6 is a schematic illustration of the data output of the antilog amplifier in relation to the density of the oilfield fluid being measured, according to one embodiment of the current application.

In this way, the data acquisition system 180 used in the prior art system 100 in association with the radioactive densitometer 140 (see FIG. 1) can be directly implemented in the current system 200 with little or no modification. This is because the radiation signal detected in the prior art system 100 is exponentially attenuated after it passes through the oilfield fluid, while the mass signal of the current system 200 remains proportional to the density of the oilfield fluid. By applying the antilog amplification, the mass signal of the current system 200 (as shown in FIG. 5 in the form of a linear curve) is transformed into an exponential signal (as shown in FIG. 6 in the form of an exponential curve). The exponential signal can then be fed into the prior art data acquisition system 180 and directly interpreted by the prior art data acquisition system 180. Therefore, significant cost saving can be achieved when switching from the radiation based densitometer system 100 as in the prior art to the non-radiation based densitometer system 200 as in the current application.

In one embodiment, the system 200 of the current application is deployed at an offshore location such as a vessel or an oil rig for conducting an oilfield operation offshore. In another embodiment, the system 200 of the current application is deployed at a land location such as on a truck, on a skid, or simply on the ground of a wellsite, for conducting an oilfield operation on the land. Furthermore, in one embodiment, the system 200 of the current application is deployed on the low pressure end (e.g. 0-200 psi) of an oilfield fluid system. In another embodiment, the system 200 of the current application is deployed on the high pressure end (e.g. 500-20,000 psi) of an oilfield fluid system. Other variations as also possible.

It should be noted that although the above description is set forth in the context of conducting a san control operation in an oilfield, embodiments of the current application are also applicable to other oilfield operations including, but not limited to, cementing, drilling, hydraulic fracturing, logging, working over, acid or other stimulation, production, and so on. Moreover, embodiments of the current application may also be applicable to other industries as well, such as construction, manufacture, transportation, just to name a few.

The preceding description has been presented with reference to some illustrative embodiments of the current application. Persons skilled in the art and technology to which this application pertains will appreciate that alterations and changes in the described structures and methods of operation can be practiced without meaningfully departing from the principle, and scope of this application. Accordingly, the foregoing description should not be read as pertaining only to the precise structures described and shown in the accompanying drawings, but rather should be read as consistent with and as support for the following claims, which are to have their fullest and fairest scope.

Furthermore, none of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC §112 unless the exact words "means for" are followed by a participle. The claims as filed are intended to be as comprehensive as possible, and NO subject matter is intentionally relinquished, dedicated, or abandoned.

We claim:

1. A non-radioactive densitometer system, comprising: a curved tube containing an oilfield fluid; a mass measuring device connected to the curved tube and configured to measure a mass of the curved tube and the oilfield fluid; a data acquisition system connected to the mass measuring device; an antilog amplifier connected between the mass measuring device and the data acquisition system, the antilog amplifier configured to transform the measured mass into an exponential value for input into the data acquisition system; and the data acquisition system is configured to calculate a density of the oilfield fluid in the curved tube based on the exponential value.

2. The non-radioactive densitometer system of claim 1, wherein the antilog amplifier is configured to transform the measured mass into the exponential value by applying the following equation: Iout=a×Exp(b×mof) (Equation III) wherein, Iout is a signal output from the antilog amplifier; a and b are constants; mof is the mass of the curved tube filled with the oilfield fluid minus the mass of the curved tube when empty.

3. The non-radioactive densitometer system of claim 1, wherein the oilfield fluid is proppant slurry.

4. The non-radioactive densitometer system of claim 1, wherein the curved tube is substantially in the form of a "U" or "V" shape.

5. The non-radioactive densitometer system of claim 1, wherein the curved tube occupies a substantially horizontal plane.

6. The non-radioactive densitometer system of claim 1, wherein the mass measuring device is a load cell.

7. The non-radioactive densitometer system of claim 6, wherein the load cell is an extension load cell.

8. The non-radioactive densitometer system of claim 7, wherein the extension load cell is connected to a tripod on one end and to the curved tube on the other end.

9. A method for measuring a density of an oilfield fluid, comprising: providing a curved tube at an oilfield; filling the curved tube with an oilfield fluid; measuring a mass of the curved tube filled with the oilfield fluid; conducting an exponential transformation of the mass of the curved tube filled with the oilfield fluid before calculating the density of the oilfield fluid and calculating a density of the oilfield fluid based on the exponential transformation of the measured mass.

10. The method of claim 9, wherein the exponential transformation is performed by applying the following equation:

$$I_{out}=a \times \text{Exp}(b \times m_{of}) \quad \text{(Equation III)}$$

wherein,
$I_{out}$ is a signal output from the antilog amplifier;
a and b are constants;
$m_{of}$ is the mass of the curved tube filled with the oilfield fluid minus the mass of the curved tube when empty.

11. The method of claim 9, wherein the oilfield fluid is proppant slurry.

12. The method of claim 9, wherein the curved tube is substantially in the form of a "U" or "V" shape.

13. The method of claim 9, wherein the curved tube occupies a substantially horizontal plane.

14. A non-radioactive densitometer apparatus, comprising: a curved tube containing an oilfield fluid therein; a load cell connected to the curved tube and configured to measure a mass of the curved tube and the oilfield fluid; a computer system connected to the load cell; and an antilog amplifier connected between the load cell and the computer system; the antilog amplifier configured to transform the measured mass into an exponential value for input into the computer system, the computer system configured to calculate a density of the oilfield fluid contained in the curved tube based on the exponential value.

15. The non-radioactive densitometer apparatus of claim 14, wherein the exponential transformation is performed by applying the following equation: Iout=a×Exp(b×mof) (Equation III) wherein, Iout is a signal output from the antilog amplifier; a and b are constants; mof is the mass of the curved tube filled with the oilfield fluid minus the mass of the curved tube when empty.

16. The non-radioactive densitometer apparatus of claim 14, wherein the oilfield fluid is proppant slurry.

* * * * *